(12) United States Patent
Zamani

(10) Patent No.: US 6,200,286 B1
(45) Date of Patent: Mar. 13, 2001

(54) PREFORMED MEMBER HAVING RAISED CONTACT FEATURE AND WRIST BRACE USING SAME

(76) Inventor: M. Hashem Zamani, 10633 Pot Spring Rd., Cockeysville, MD (US) 21030

(*) Notice: Subject to any disclaimer, the term of this patent is extended or adjusted under 35 U.S.C. 154(b) by 0 days.

(21) Appl. No.: 09/095,844

(22) Filed: Jun. 11, 1998

(51) Int. Cl.[7] ............................. A61F 5/00; A61F 13/00
(52) U.S. Cl. ............................. 602/64; 602/20; 602/21; 602/60; 602/62
(58) Field of Search .................. 473/59–63; 428/44–50; 2/16, 20, 159–161.8; 602/20, 21, 22, 60, 69, 13

(56) References Cited

U.S. PATENT DOCUMENTS

| | | |
|---|---|---|
| 1,797,057 | 3/1931 | Foulke . |
| 3,703,894 | 11/1972 | Galloway et al. . |
| 4,013,070 | 3/1977 | Harroff . |
| 4,584,993 | 4/1986 | Nelson . |
| 5,014,689 | 5/1991 | Meunchen et al. . |
| 5,267,943 | 12/1993 | Dancyger ................................. 602/5 |
| 5,350,418 | 9/1994 | Janevski et al. ...................... 607/111 |
| 5,376,066 | 12/1994 | Phillips et al. ......................... 602/21 |
| 5,427,577 | 6/1995 | Picchietti et al. ....................... 473/59 |
| 5,484,392 | 1/1996 | Sydor et al. ............................. 602/5 |
| 5,513,657 | 5/1996 | Nelson ................................. 128/879 |
| 5,526,531 | 6/1996 | Olson et al. ............................... 2/16 |
| 5,540,735 | 7/1996 | Wingrove ............................... 607/46 |
| 5,702,355 | 12/1997 | Repice et al. ........................... 602/21 |
| 5,746,707 | 5/1998 | Eck ......................................... 602/21 |
| 5,759,166 | 6/1998 | Nelson et al. .......................... 602/21 |
| 5,769,804 | 6/1998 | Harrison et al. ........................ 602/21 |
| 5,810,753 | * 9/1998 | Eberbach ........................... 602/20 X |

OTHER PUBLICATIONS

How Handwel Gloves Work, Handwel (visited Feb. 5, 1998) <http://www.interlog.com/~paltron/handwel/html/how_.html>.
How Does It Work, Alpha–Med Technologies (visited Oct. 16, 1998) <http://www.alphaglove.com/howdoes.htm>.
The Alpha Glove, AlphaGlove, (visited Feb. 5, 1998) <http:\\alphaglove.com/index.htm>.
Products Available, Alpha–Med Technologies (visited Oct. 16, 1998) <http:\\www.alphaglove.com/products.htm>.
Products, Products That Help Prevent and Ease Carpal Tunnel Syndrome (visited Jan. 5, 1998) <http:\\www.carpal–tunnel.com/products.htm>.
OccuMitts, OccuMitts & OccuMitts Plus, OccuNomix Internat'l, Inc., Port Jefferson Station, NY (facsimile reception date Feb. 6, 1998).

* cited by examiner

*Primary Examiner*—Kim M. Lee
(74) *Attorney, Agent, or Firm*—Fitzpatrick, Cella, Harper & Scinto

(57) ABSTRACT

A wrist brace includes a sleeve and a preformed member where the preformed member includes one or more raised contact portions extending longitudinally along the preformed member. When secured to a user's hand, wrist, and distal forearm, the raised contact portions abut portions of the hand, wrist, and distal forearm and prevents pressure from being applied to the median nerve against the carpal tunnel of the user.

31 Claims, 5 Drawing Sheets

US 6,200,286 B1

PREFORMED MEMBER HAVING RAISED CONTACT FEATURE AND WRIST BRACE USING SAME

FIELD OF THE INVENTION

The present invention relates to a preformed member for use with a wrist brace and a wrist brace using the same, and more particularly to a device that dictates and stabilizes the position of a user's hand and wrist relative to the user's distal forearm and protects the user's median nerve.

BACKGROUND

Carpal tunnel syndrome is a disease within a larger group of musculoskeletal system disorders known as repetitive strain disorders or cumulative trauma disorders. These disorders arise from injuries caused by the buildup of daily damage from repetitive motions and impacts. The injuries can lead to problems in the fingers, hands, wrists, and forearms. These problems include numbness, burning or tingling sensations, pain, restricted movement, stiffness, muscle atrophy, weakness, and clumsiness. In more advanced cases, the symptoms can also manifest themselves in the upper arms, shoulders, and neck.

The repetitive motions or impacts that cause carpal tunnel syndrome can occur during such common activities as typing, operating pneumatic devices (e.g., jack-hammers and nail guns), knitting, and playing musical instruments.

Each individual movement or impact may cause damage that is naturally repaired by the mechanisms of healthy tissue. When the motions or impacts occur repeatedly, the damage compounds making it more difficult for the body to repair itself. Over time a restricted blood supply to these areas causes repetitive strain disorders, such as tendinitis and carpal tunnel syndrome. Tendinitis is an inflammation of the tendons, whereas carpal tunnel syndrome occurs when the median nerve is pinched or irritated in the carpal tunnel in the wrist.

The wrist has an arched structure of bones that combine with the transverse carpal ligament to define an opening through the wrist known as the carpal tunnel. The median nerve, which controls the first three to four fingers, and the flexor tendons, which attach to the bones in the fingers, all extend through the carpal tunnel into the hand.

Repetitively worked, flexor tendons eventually will become irritated. This irritation can cause an inflammation of the flexor tendons. Consequently, the flexor tendons will swell and thicken from overuse. The bones and ligament forming the carpal tunnel are not able to either adequately stretch or expand to accommodate the swollen and thickened flexor tendons. Thus, the inflammation or swelling of the flexor tendons squeezes the median nerve against the transverse carpal ligament, thereby exerting pressure on the median nerve. When the pressure becomes great enough, the median nerve cannot function normally and the above-noted problems and symptoms occur.

Other events can lead to increased pressure on the median nerve. The pressure can be caused by the swelling of the median nerve itself, arthritis, or mechanical pressures (i.e., outside stresses, such as vibration or pressure, or the force of fractured wrist bones). In each scenario, the increased pressure on the median nerve can cause the pinching, irritation, and inflammation that leads to carpal tunnel syndrome.

The problems that accompany carpal tunnel syndrome can be debilitating to sufferers. Often individuals with the syndrome awake from their sleep due to sharp pains shooting up their arms. Sufferers also find it increasingly difficult to perform simple tasks involving manual dexterity, such as grasping objects, writing, typing, opening jars, buttoning clothes, and tying shoelaces. This results in the inability of of sufferers to function not only in the home but also in the workplace.

There are many known devices and methods available for preventing and treating carpal tunnel syndrome.

One effective means of treatment is to avoid the activity that produced the carpal tunnel syndrome. However, this treatment is often impractical or impossible for most people, such as where the activity or activities are directly related to their livelihoods.

Anti-inflammatory medicines, certain vitamins, and cortisone injections have been used with varying degrees of success to alleviate the symptoms of carpal tunnel syndrome.

Strict posture requirements and frequent breaks from repetitive movement tasks and repetitive impact tasks are also suggested for preventing repetitive strain disorders. However, many workers are unavoidably subjected for extended periods of time to the highly repetitive motions and impacts that cause these disorders.

Once the injury manifests itself and is otherwise not responsive to treatment, surgery is available to correct the problem. Corrective surgery, sometimes referred to as a carpal tunnel release, requires cutting the tendons surrounding the nerve to alleviate the pressure. This procedure is expensive and risks further damaging the median nerve.

Wrist braces have been used to both prevent and treat carpal tunnel syndrome. Such braces use rigid stays to secure the hand, wrist, and distal forearm at an angle that reduces the stress and pressure on the median nerve. However, the braces currently on the market utilize stays that apply direct pressure to a portion of the hand overlying the carpal tunnel. Thus, the stays can actually add harmful pressure to the median nerve.

Thus, there is a need for a wrist brace that secures the hand, wrist and distal forearm but does not put any additional pressure on the carpal tunnel or median nerve.

U.S. Pat. No. 5,484,392 issued to Snyder et al. discloses a wrist support with a stay having an opening in its interior and flexible slits around its edges. The opening releases compression on the median nerve. The slits provide needed flexibility at the outer portions of the brace to improve movement. However, the stay of Snyder et al., must be wide enough to allow for both an interior opening wide enough to avoid contacting the carpal tunnel and lateral sides wide enough to adequately support the hand and wrist. Accordingly, the size of the brace of Synder et al., may prove to be cumbersome and make it difficult to perform certain activities making such a brace an impractical choice for many users suffering from carpal tunnel syndrome. Further, the stay of Snyder et al. is somewhat complex in design, adding to the cost of manufacture.

SUMMARY OF THE INVENTION

The wrist brace of the present invention addresses the foregoing needs in the art by providing a preformed member shaped to support a user's hand, wrist, and distal forearm (also known as the distal radius) in a position such that pressure exerted by the median nerve against the carpal tunnel is minimized. The preformed member includes raised cushions or contact portions running longitudinally along the interior side of the preformed member and abutting the palm of a user when it is being worn.

The raised contact portions can be formed of elongated, semi-tubular cushions, such as hemispherical cushions, inflatable bladders, or other like arrangements, which may be attached to the preformed member. The raised contact portions, which can be separately formed or, as part of a single, elongated, u-shaped raised contact portion. The separate contact portions on the elgonated, longitudinal sides of u-shaped raised contact portion are spaced apart from each other such that they lie on opposing sides of the user's carpal tunnel and provide a pressure-reduced zone directly over the median nerve.

Alternatively, the raised contact portions may be integrally formed with the preformed member.

The preformed member can be removably fastened in a pocket on a sleeve or fastening system which stretches or wraps around the user's hand, wrist, and distal forearm to secure the interior side of preformed member to the ventral side of the hand, i.e., the palm, wrist, and distal forearm.

Alternatively, the performed member can be removably fastened directly to the user's hand, wrist, and distal forearm using straps, tape, or a bandage, such as an ACE® bandage.

The inventive wrist brace provides the necessary support to the hand, wrist, and distal forearm to secure the wrist in a position best suited for preventing pressure on the median nerve. At the same time, the raised contact portions prevent the preformed member from putting any additional pressure on the carpal tunnel or median nerve.

These and other objects, features, and advantages will be apparent from the following discussion and with reference to the appended drawings, in which like reference characters refer to like elements throughout.

DETAILED DESCRIPTION OF THE PREFERRED EMBODIMENT

Figure 1:
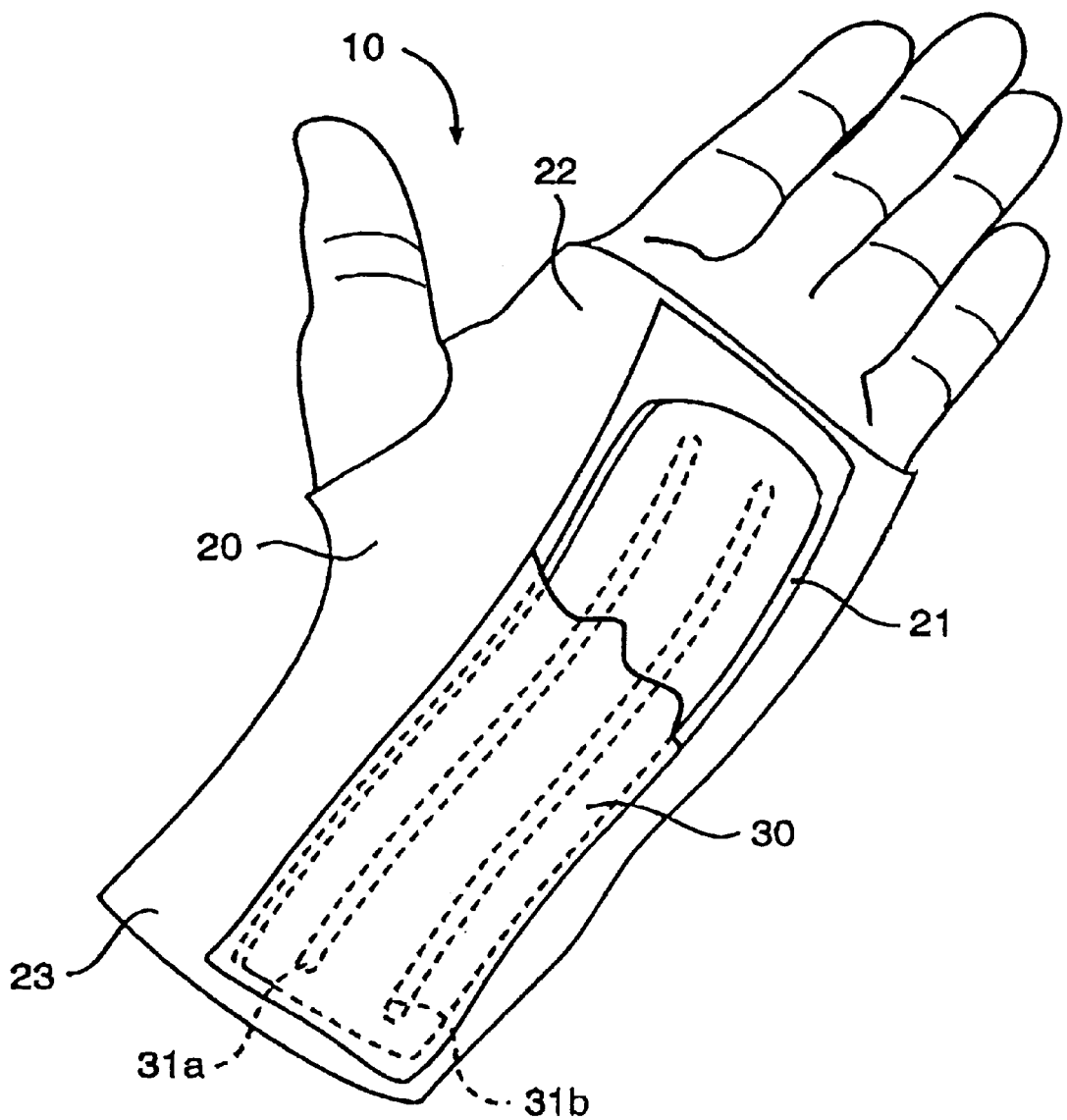
FIG. 1 is a partial cut-away, perspective view of a wrist brace according to an embodiment of the present invention, as worn by a user.

An embodiment of the present invention, relating to what is generally referred to as a wrist brace herein for convenience, is shown in FIG. 1. The wrist brace 10 in general includes a sleeve 20, which is worn by a user as shown, and a preformed member 30, which is attached to the sleeve 20. When the wrist brace 10 is worn by the user, the preformed member 30 extends substantially longitudinally from a portion of the sleeve 20 overlying the user's distal forearm to a portion of the sleeve overlying the user's palm. At least two raised contact portions 31a, 31b are provided to reduce the pressure exerted by the preformed member 30 on the user's carpal tunnel.

Figure 2:
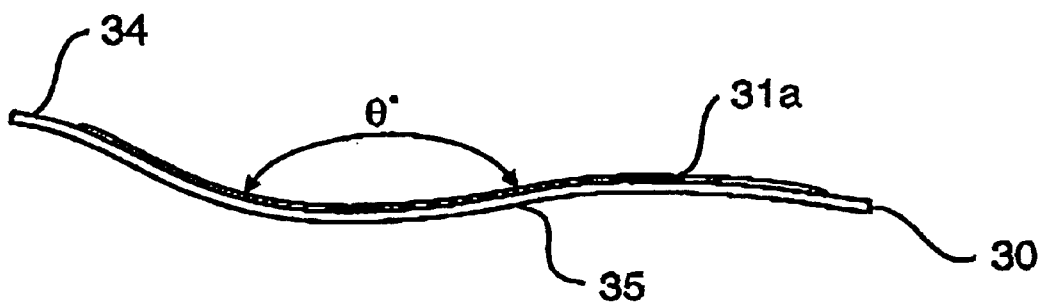
FIG. 2 is a side view of the preformed member of the wrist brace of FIG. 1.
Figure 3:
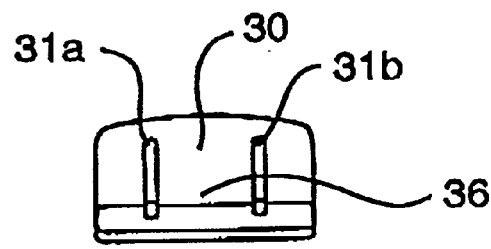
FIG. 3 is a longitudinal view of the preformed member of the wrist brace of FIG. 1.
Figure 4:
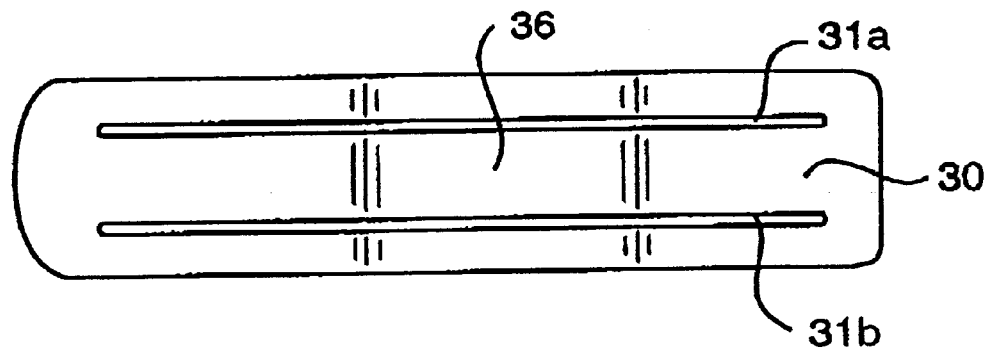
FIG. 4 is a top view of the preformed member of the wrist brace of FIG. 1.

As shown in FIG. 2, the preformed member 30 has an interior side 34 and an exterior side 35. When worn in the sleeve 20, the interior side 34 of the preformed member 30 faces toward the user's palm, wrist, and distal forearm. The preformed member 30 is preferably anatomically curved at an appropriate angle θ with respect to the user's palm and distal forearm to support a user's palm, wrist, and distal forearm in a posture such that the user's median nerve is not pinched in the carpal tunnel. Being shaped in this manner, when the wrist brace 10 is worn, the preformed member 30 supports the user's hand, wrist and distal forearm in a position that reduces the pressure on the carpal tunnel and median nerve. The angle θ is typically set within the range from approximately 15° to slightly over 30°, and in a preferred embodiment is approximately 30°.

The preformed member 30 can be made of metal, plastic, or any other suitable material that can provide adequate rigidity and is otherwise suitable for use in a medical appliance.

In the embodiment shown in FIGS. 1 through 4, the preformed member 30 contains a pair of raised contact portions 31a, 31b, but more than two raised contact portions may also be used. The raised contact portions 31a, 31b extend laterally along the interior side 34 of the preformed member 30. The raised contact portions 31a, 31b are laterally spaced apart from one another such that, when the wrist brace 10 is worn by a user, the raised contact portions 31a, 31b lie contralateral to the user's carpal tunnel and median nerve. In the embodiment shown in FIG. 4, the raised contact portions 31a, 31b lie substantially parallel with each other. The raised contact portions 31a, 31b, however, need not be parallel but can also be ergonomically curved to fit the contours of a user's palm, wrist, and distal forearm.

The purpose of the raised contact portions 31a, 31b, when properly positioned, is to provide a contact area that abuts against a user's palm, wrist, and distal forearm thereby creating a space between a center portion of the preformed member and the user's palm, wrist, and distal forearm. This arrangement absorbs pressure that would otherwise be exerted by the preformed member 30 against the user's carpal tunnel and median nerve. Accordingly, the pair of raised contact portions, 31a, 31b in FIG. 4, or two most central contact portions 31a, 31b when a greater plurality of contact portions, is used, lie on opposing sides of (or contralateral to) the user's carpal tunnel. This dampens or prevents the contact pressure exerted by the center portion 36 of the preformed member 30 against the user's palm, wrist, and distal forearm.

In one embodiment, the raised contact portions 31a, 31b are formed from inflatable bladders. Other suitable embodiments include, but are not limited to, raised contact portions 31a, 31b formed of a pliable, cushioned, or padded materials, such as plastic or rubber cushions. The raised contact portions can be secured to the preformed member by any adhesive known in the art not to degrade the material chosen for the raised contact portions and the preformed member, and which is also acceptable for prolonged exposure to the user's skin. Alternatively, the raised contact portions 31a, 31b may be contours integrally formed in the preformed member 30, such as by molding, stamping, pressing, or the like.

The sleeve itself can be configured according to any of a number of designs well known in the art, so long as it adequately secures the performed member 30 in place against the user's hand, wrist, and distal forearm. Referring to the particular type of sleeve 20 shown in FIGS. 1 and 5 through 7, the sleeve 20, when worn, can be characterized as having a distal end portion 22 and a proximal end portion 23, and having a dorsal portion 24 and a ventral portion 25. The sleeve 20 is formed of any of a number of materials that have proven to be suitable to be fastened around the hand, wrist, and distal forearm of the user. Alternatively, the "sleeve" 20 may take the form a flat sheet of material that is wrapped around the hand, wrist, and distal forearm. The sleeve 20 is adapted to hold the interior side 34 of preformed member 30 securely against the ventral side of the hand, wrist, and distal forearm. The user pulls the sleeve 20 over the hand, wrist, and distal forearm or wraps these areas with the wrist brace 10. If necessary, the sleeve 20 can be secured with one or more fasteners. The sleeve 20 or sheet of material can be tightened into position with any known fastener, including snaps, laces, clips, pins, hook-and-loop fasteners, such as VELCRO® fasteners, and elastic materials.

Figure 7:
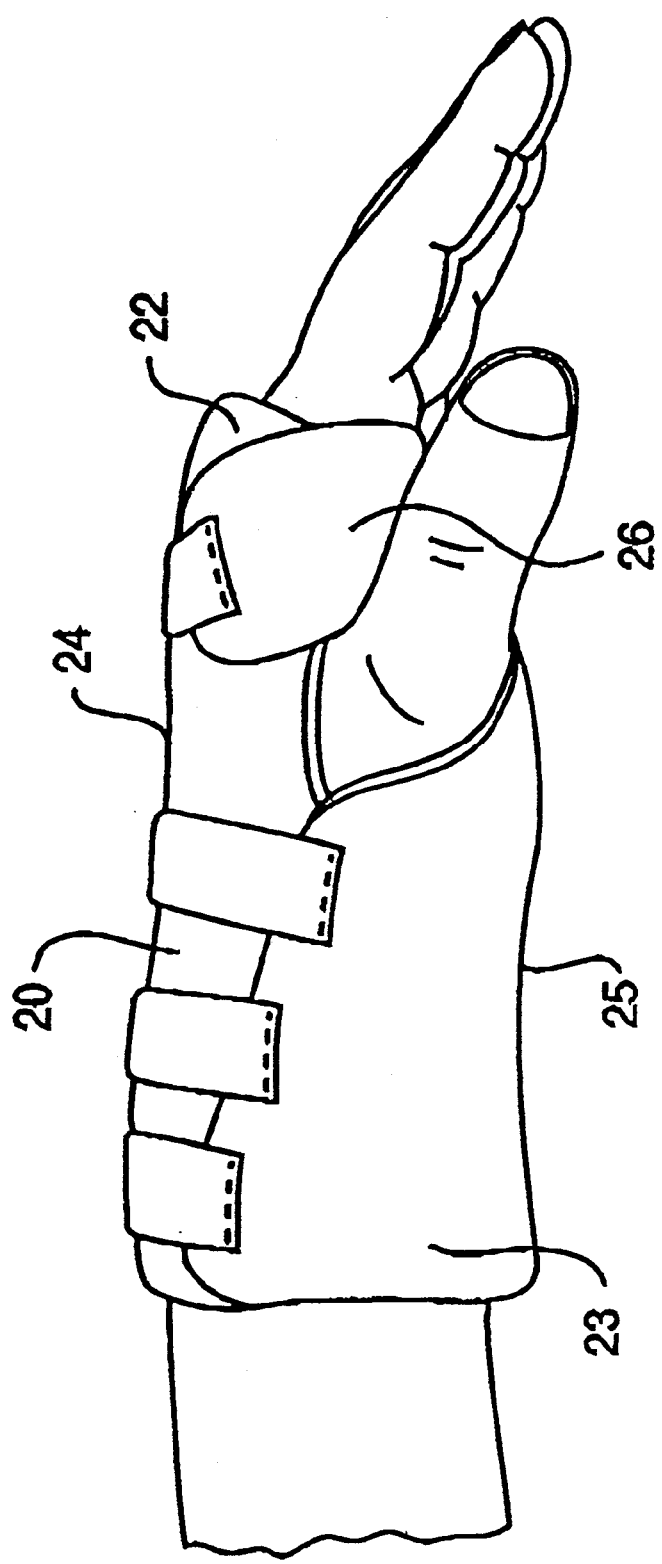
FIG. 7 is a side view of the wrist brace shown in FIG. 1.

Referring to FIG. 7, a strap portion 26 of the sleeve 20 can be provided to prevent the wrist brace 10 from sliding up a user's forearm. The strap portion 26 extends between a user's thumb and forefinger, connecting the dorsal portion 24 and the ventral portion 25 of the sleeve 20 or sheet of material. When the wrist brace 10 is properly worn, the strap portion 26 is in contact with the web of skin extending between the user's thumb and the forefinger.

The strap portion 26 can be a continuous portion of the material used for the sleeve 20 or the flat sheet of material or can be formed from a fastening system. A particular fastening systems includes a piece of material continuous with either of the dorsal portion 24 or ventral portion 25 and having an opposite free end. Alternatively, both ends may be free. The free end or ends may be releasably secured to the sleeve 20 or flat sheet of material by any of a number of suitable fasteners including snaps, hook-and-loop fasteners, clips, pins, and laces. The strap portion 26 can also be an elastic material stretched between the dorsal portion and ventral portion of the sleeve 20 or sheet of material.

In addition, the sleeve 20 can include finger slots or openings at the distal end portion 22. These slots or openings can be formed through pieces of material, connecting the dorsal portion and ventral portion of the sleeve 20.

In one embodiment the preformed member 30 is held in a pocket 21 on the ventral side of the sleeve 20 or sheet of material. In the illustrated embodiment, the preformed member 30 can be removably secured in the pocket 21 by a fastenable cover to prevent the preformed member 30 from falling out. In this manner, the preformed member 30 can be removed from the pocket 21 in order to launder the sleeve 20 or the flat sheet of material.

The preformed member 30 can be secured to the sleeve 20 in a variety of other ways. For example, the preformed member 30 can be permanently attached under a patch stitched closed on all sides to the sleeve 20 or the flat sheet of material.

The preformed member 30 can also be secured without a pocket 21. It is acceptable to secure the preformed member 30 directly to the user's hand, wrist, and distal forearm. This can be achieved by placing the preformed member 30 against the user's hand, wrist, and distal forearm and then pulling the sleeve 20 into place over the preformed member 30. Alternatively, the performed member 30 can be removably fastened directly to the user's hand, wrist, and distal forearm using straps, tape, or a bandage, such as an ACE® bandage, that extend(s) circumferentially around the user's hand, wrist, and distal forearm.

Figure 5:
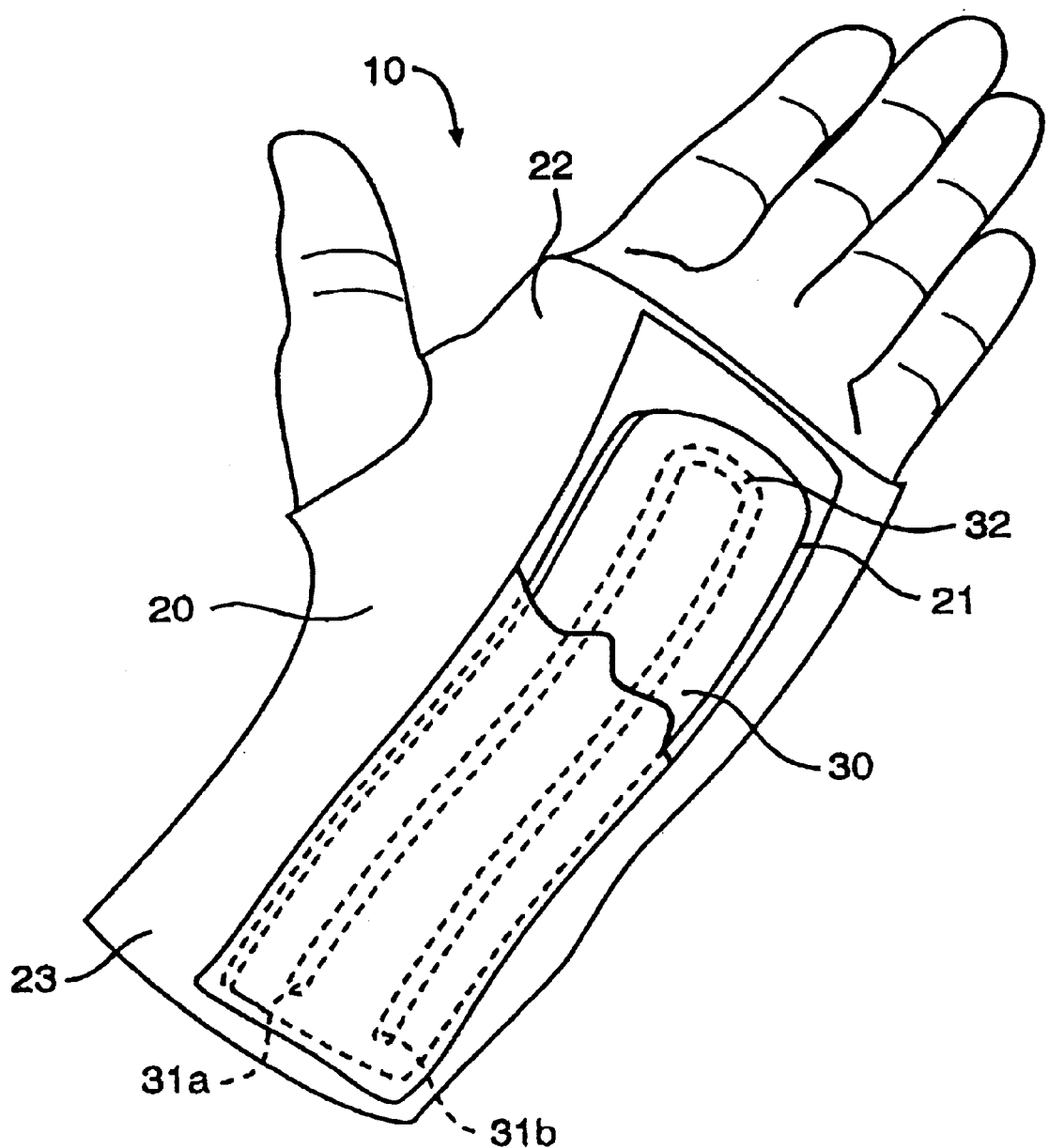
FIG. 5 is a partial cut-away, perspective view of a wrist brace according to another embodiment of the present invention.

Referring particularly to FIG. 5, another embodiment of invention is shown in which the raised contact portions 31a, 31b are integrally formed into a single, u-shaped raised contact portion integrated at either a distal end or a proximal end of the preformed member 30, or both. In a preferred embodiment the raised contact portions 31a, 31b are integrated at a distal end of the preformed member 30 by a u-shaped portion 32 thereby forming a single raised contact portion. Thus, the open end of the independent raised contact portions face the distal forearm. This orientation ensures that pressure is not exerted on the median nerve passing through the wrist.

Figure 6:
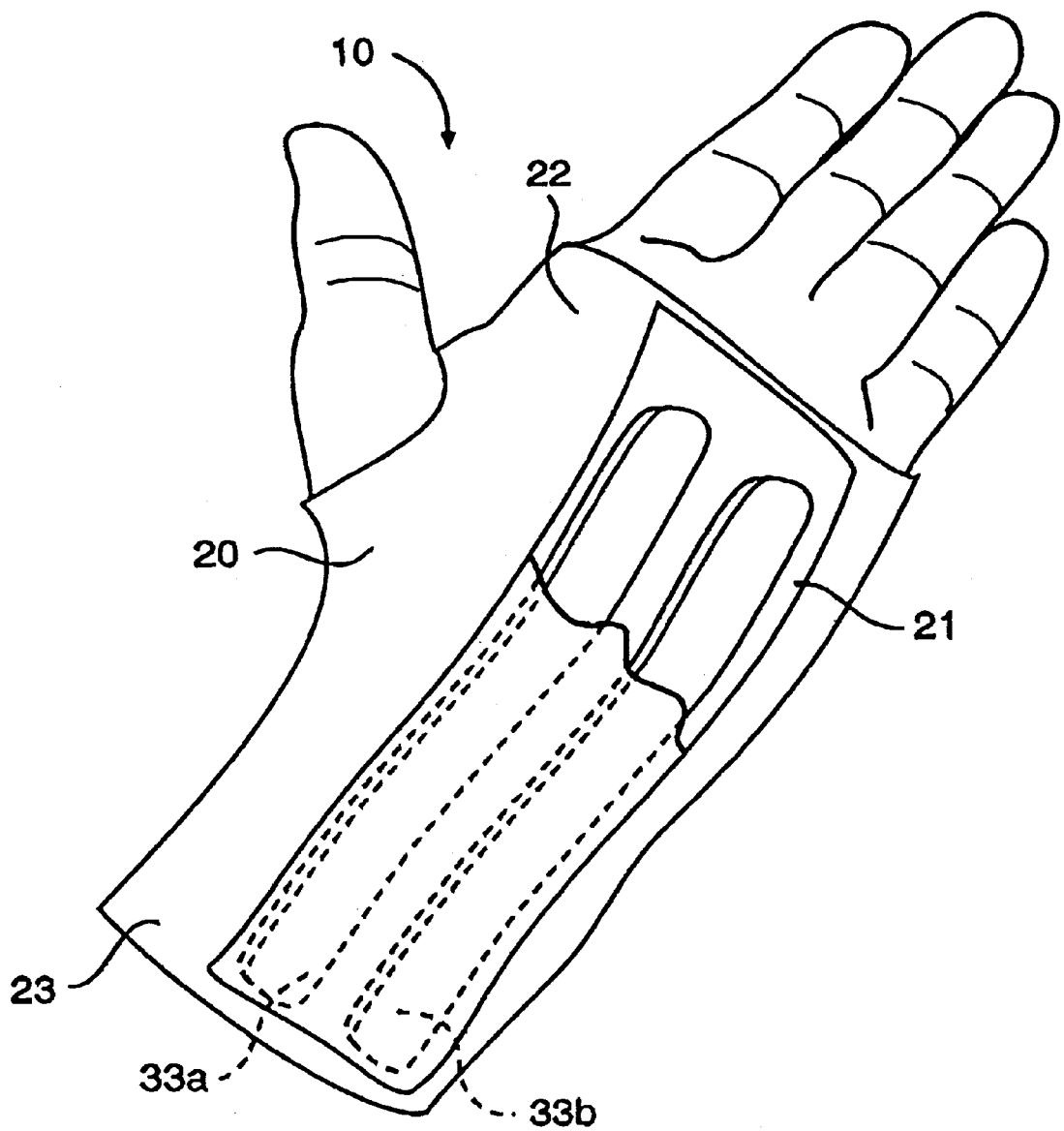
FIG. 6 is a partial cut-away, perspective view of a wrist brace according to another embodiment of the present invention.

In another embodiment, rather than using a single performed member with raised contact portions, the wrist brace 10 stabilizes a user's hand, wrist, and distal forearm by employing a plurality of substantially rigid contact portions 33a, 33b, as shown in FIG. 6. When worn in a wrist brace 10, the contact portions 33a, 33b extend longitudinally from a user's palm to the distal forearm. The rigid contact members 33a, 33b can be anatomically curved similarly to the above-described preformed member 30 in order to support the hand, wrist, and distal forearm in a position causing the least amount of pressure on the median nerve. Rather than being connected to a preformed member 30, each contact portion is independent of the others. The raised contact portions 33a, 33b are held in position by a securing material that forms stitched patches, individual pockets, or other suitable securing means. The securing material secures the raised contact portions 33a, 33b at positions spaced apart from one another such that, when being worn by a user, the rigid contact portions 33a, 33b lie contralaterally to the user's carpal tunnel and median hand. The raised contact members 33a, 33b can include padding material for the user's comfort. The contact portions 33a, 33b can also be joined to form u-shaped portions similarly to the raised contact portions 31a, 31b of the above-described preformed member 30.

Although FIG. 6 shows two raised contact portions 33a, 33b, another embodiment features a plurality of raised contact portions disposed, preferably in pairs, contralaterally to the user's carpal tunnel. Such a plurality of raised contact portions may comprise either the simple elongated contact portions or the u-shaped raised contact portions.

The raised contact portions 33a, 33b and securing material can be secured to the ventral side of the user's hand, wrist, and distal forearm by any of the to means or devices used to secure the preformed member 30 of the first embodiment.

While in the foregoing discussion, a detailed description of specific embodiments of the invention has been set forth for the purposes of illustration. It will be understood that many of the details herein given can be varied considerably by those skilled in the art without departing from the spirit and scope of the claimed invention.

What is claimed is:

1. A preformed member for use with a wrist brace, comprising:
   a substantially rigid member anatomically curved to, when worn with the wristrace by a user, support the user's hand, wrist, and distal forearm in a position so as to reduce pressure exerted on the user's median nerve within the user's carpal tunnel; and
   raised contact portions extending longitudinally along an interior side of said rigid member, said raised contact portions being laterally displaced on opposing sides of the carpal tunnel when said performed member is being worn with the wrist brace by the user.

2. The preformed member of claim 1 wherein said raised contact portions comprise a u-shaped portion and two longitudinal side portions spaced apart from each other, said u-shaped portion and said side portions forming a contiguous, unitary, raised contact portion.

3. The preformed member of claim 1 wherein said substantially rigid member is shaped to conform to a desired anatomical curve between a user's palm, wrist, and distal forearm to reduce pressure being exerted on the user's median nerve in the user's carpal tunnel when the wrist brace is being worn by the user.

4. The preformed member of claim 3 wherein said substantially rigid member is shaped to support the user's palm and distal forearm at approximately a 30° angle with respect to each other.

5. The preformed member of claim 1 wherein said pair of raised contact portions are substantially parallel with one another.

6. The preformed member of claim 1 wherein each of said raised contact portions comprises an inflatable bladder.

7. The preformed member of claim 1 wherein each of said raised contact portions comprises a pliable, cushioned material.

8. The preformed member of claim 1 wherein said raised contact portions comprises a padding material.

9. The performed member of claim 1 wherein each of said raised contact portions comprises contours integrally formed with said preformed member.

10. A wrist brace comprising:
   a sleeve contoured to conform to a user's palm, wrist, and distal forearm when said wrist brace is being worm; and
   a substantially rigid preformed member having an interior side and an exterior side, said preformed member being removably securable to said sleeve so as to extend longitudinally from the user's distal forearm to the user's palm when said wrist brace is being worn, said preformed member including a pair of raised contact portions extending longitudinally along the interior side of said preformed member, said pair of raised contact portions being longitudinally spaced apart from each other so as to be contralateral to the user's carpal tunnel when said wrist brace is being worn by the user.

11. The wrist brace of claim 10 wherein said preformed member is shaped to conform to a desired anatomical curve between a user's palm, wrist, and distal forearm to reduce pressure being exerted on the user's median nerve in the user's carpal tunnel when said wrist brace is being worn by the user.

12. The wrist brace of claim 11 wherein said preformed member is shaped to support the user's palm and distal forearm at approximately a 30° angle with respect to each other.

13. The wrist brace of claim 10 wherein said pair of raised contact portions are substantially parallel with one another.

14. The wrist brace of claim 10 wherein said pair of raised contact portions are contiguous so as to form an integral, u-shaped member.

15. The wrist brace of claim 14 wherein said u-shaped member is disposed so as to be open in a direction toward the user's distal forearm.

16. The wrist brace of claim 10 wherein each of said raised contact portions comprises an inflatable bladder.

17. The wrist brace of claim 10 wherein each of said raised contact portions comprises a pliable, cushioned material.

18. The wrist brace of claim 10 wherein each of said raised contact portions comprises a padding material.

19. The performed member of claim 10 wherein each of said raised contact portions comprises contours integrally formed with said preformed member.

20. A wrist brace comprising:
   a preformed member including an interior side, a proximal end of which is configured to overlie a portion of a user's distal forearm, and a distal end which is configured to overlie a portion of the user's hand, said preformed member further including a pair of raised contact portions extending longitudinally along the interior side of said preformed member, said pair of raised contact portions being longitudinally spaced apart from each other and lying contralateral to the user's carpal tunnel when said wrist brace is being worn by the user; and
   means for securing the interior surface of said preformed member against a ventral side of the user's hand, wrist, and distal forearm.

21. The wrist race of claim 20 wherein said preformed member is shaped to maintain an anatomical curve between the user's palm and distal forearm such that a user's median nerve is not pinched within the user's carpal tunnel.

22. The wrist brace of claim 21 wherein the preformed member is shaped to support the user's palm and distal forearm at approximately a 30° angle with respect to each other.

23. The wrist brace of claim 20 wherein said pair of raised contact portions are contiguous so as to form an integral, u-shaped member.

24. The wrist brace of claim 20 wherein each of said raised contact portions comprises an inflatable bladder.

25. The wrist brace of claim 20 wherein each of said raised contact portions comprises a pliable, cushioned material.

26. The performed member of claim 20 wherein each of said raised contact portions comprises contour integrally formed with said preformed member.

27. A wrist brace comprising:
   a plurality of substantially rigid contact members, said contact members being anatomically curved to include a proximal end conforming to a ventral portion of a user's forearm and a distal end conforming to a portion of the user's palm when being worn;
   securing means for securing said contact members to a user's hand, wrist, and forearm at positions spaced apart from each other so as to extend longitudinally and contralaterally to the user's carpal tunnel; and
   a preformed member, wherein said contact members comprise contours integrally formed on a surface of said preformed member.

28. The wrist brace of claim 27 wherein at least two of said contact members are integrated at the distal end.

29. The wrist brace of claim 27 wherein each of said contact portions comprises an inflatable bladders.

30. The wrist brace of claim 27 wherein each of said contact portions comprises a pliable, cushioned material.

31. The wrist brace of claim 27 wherein each of said contact portions each comprise a padding material.

* * * * *